US011494849B1

(12) United States Patent
Sardegna

(10) Patent No.: US 11,494,849 B1
(45) Date of Patent: Nov. 8, 2022

(54) SYSTEMS AND METHODS FOR DISTRIBUTED ARCHITECTURES TO PROVIDE SCALABLE INFRASTRUCTURE IN REPRICING SYSTEMS

(71) Applicant: Evernorth Strategic Development, Inc., St. Louis, MO (US)

(72) Inventor: Christopher Sardegna, Brooklyn, NY (US)

(73) Assignee: Evernorth Strategic Development, Inc., St. Louis, MO (US)

( * ) Notice: Subject to any disclaimer, the term of this patent is extended or adjusted under 35 U.S.C. 154(b) by 0 days.

(21) Appl. No.: 17/366,880

(22) Filed: Jul. 2, 2021

(51) Int. Cl.
*G06Q 40/08* (2012.01)
*G06F 16/23* (2019.01)
*G06F 16/2453* (2019.01)
*G16H 40/20* (2018.01)

(52) U.S. Cl.
CPC ......... *G06Q 40/08* (2013.01); *G06F 16/2379* (2019.01); *G06F 16/24539* (2019.01); *G16H 40/20* (2018.01)

(58) Field of Classification Search
CPC .............. G06Q 40/08; G06F 16/2379; G06F 16/24539; G16H 40/20
USPC ...................................................... 705/3–44
See application file for complete search history.

(56) References Cited

U.S. PATENT DOCUMENTS

| 6,792,410 | B1 * | 9/2004 | Donovan | ............... | G06Q 40/02 |
| | | | | | 705/4 |
| 7,447,652 | B2 | 11/2008 | Keyes | | |
| 8,621,549 | B2 | 12/2013 | Lim | | |
| 8,677,499 | B2 | 3/2014 | Lim | | |
| 9,942,271 | B2 | 4/2018 | Lim | | |
| 10,032,195 | B2 | 7/2018 | Abbassi | | |
| 2005/0033612 | A1 * | 2/2005 | Donovan | ............... | G06Q 40/08 |
| | | | | | 705/4 |
| 2005/0071249 | A1 * | 3/2005 | Nix | ........................ | G06Q 30/06 |
| | | | | | 705/26.8 |

(Continued)

FOREIGN PATENT DOCUMENTS

WO   WO-2015192106 A1 * 12/2015   ......... G06Q 30/0206

OTHER PUBLICATIONS

Schaumans et al., "Entry and regulation: evidence from health care professions", RAND Journal of Economics 39.4: 949(24), Jan.-Mar. (Year: 2008).*

*Primary Examiner* — Frantzy Poinvil
(74) *Attorney, Agent, or Firm* — Stinson LLP

(57) ABSTRACT

A query processing server for providing scalable architectures in repricing is provided. The query processing server includes a gateway platform for processing communications and a repricing engine. The query processing server processor is configured to receive a repricing request from a frontend server. The query processing server processor is also configured to define a set of repricing periods. The query processing server processor is further configured to transmit a creation instruction to the repricing database server to create a repricing status database and queue. The query processing server processor is also configured to determine a set of claims data queries for execution based on the set of scenario data and to query the repricing database server with the set of claims data queries. The query processing server processor is configured to perform a repricing analysis using the set of claims data responses and the set of repricing periods.

20 Claims, 6 Drawing Sheets

(56) References Cited

U.S. PATENT DOCUMENTS

| | | | |
|---|---|---|---|
| 2006/0206438 A1* | 9/2006 | Sakaue | G06Q 30/08 |
| | | | 705/37 |
| 2007/0282824 A1* | 12/2007 | Ellingsworth | G06F 16/313 |
| | | | 707/999.005 |
| 2013/0166340 A1* | 6/2013 | Salame | G06Q 10/06 |
| | | | 705/7.14 |
| 2014/0081710 A1 | 3/2014 | Rabie | |
| 2017/0161651 A1 | 6/2017 | Demarchi | |
| 2018/0075497 A1* | 3/2018 | Beguerie | G06Q 30/0283 |
| 2018/0121857 A1* | 5/2018 | Gutman | G16H 15/00 |
| 2018/0165757 A1 | 6/2018 | Gelber | |
| 2018/0240195 A1* | 8/2018 | Bogle | G16H 40/20 |
| 2020/0244680 A1 | 7/2020 | Brandel | |

\* cited by examiner

SYSTEMS AND METHODS FOR DISTRIBUTED ARCHITECTURES TO PROVIDE SCALABLE INFRASTRUCTURE IN REPRICING SYSTEMS

FIELD

The field generally relates to distributed system architectures to allow for increased concurrency, throughput, and scaling and to provide implementations of idempotent and asynchronous logic for use in queries and repricing models.

BACKGROUND

Technological architectures used to support business tools often face challenges in scalability, throughput, and efficiency. As the business needs develop, such challenges often become barriers to effective functioning of the business tools. Notably, as business needs increase, the wait time, resource cost, and financial cost of the business tools increase significantly while the reliability of the business tools may be negatively impacted.

In some architectures, one notable problem is a scalability limitation imposed by the available central processor units ("CPUs") leading to a condition known as "CPU bounding" wherein the rate of processing by a business tool is limited by the speed of available CPUs. This problem may further implicate or relate to a problem of excess utilization of memory. Collectively, these resource issues may lead to further performance difficulties that may negatively impact the provision, scalability, and stability of the business tools at issue.

In particular, some business tools such as repricing tools and related pricing tools face such problems of scale, throughput, and efficiency, particularly when used in complex data centers for insurance companies and related businesses. Use of these business tools (and other similar ones) is often characterized by a requirement to process massive volumes of data ranging from tens of thousands of records to many millions of records. Because of the data processing needs, the burden associated with scale, throughput, and efficiency problems is compounded. From a technical perspective, the combination of the business utilization and the technical limitations can lead to processing delays and even failures.

In view of the above technological challenges, systems and methods are desired for improving distributed system architectures to allow for increased concurrency, throughput, and scaling and to provide implementations of idempotent and asynchronous logic for use in and with query intensive business tools including repricing and pricing applications.

BRIEF SUMMARY

In one aspect, a computing network for providing scalable architectures is provided. The computing network includes a frontend server further including a frontend server processor and a frontend server memory. The computing network also includes a query processing server further including a query processing server processor and a query processing server memory. The query processing server includes a gateway platform for processing communications and a repricing engine. The computing network also includes a repricing database server further including a repricing database processor and a repricing database memory. The frontend server, the query processing server, and the repricing database server are all in networked communication with one another. The query processing server processor is configured to receive, at the gateway platform, a repricing request from the frontend server. The repricing request includes a set of scenario data associated with a repricing scenario. The set of scenario data includes a set of pricing rules and a set of conditional assumptions. The set of pricing rules and the set of conditional assumptions include corresponding timings. The query processing server processor is also configured to define a set of repricing periods based on the corresponding timings for the pricing rules and the set of conditional assumptions. The query processing server processor is further configured to transmit a creation instruction to the repricing database server to create a repricing status database defined based on the set of scenario data and the set of repricing periods. The query processing server processor is also configured to determine a set of claims data queries for execution based on the set of scenario data. The query processing server processor is further configured to query the repricing database server with the set of claims data queries. The query processing server processor is also configured to receive a set of claims data responses responsive to the set of claims data queries. Upon receiving the set of claims data responses, the query processing server processor is further configured to transmit an update instruction to the repricing status database based on the set of claims data responses. Upon determining that the repricing status database indicates that the repricing is complete, the query processing server processor is configured to perform a repricing analysis using the set of claims data responses and the set of repricing periods.

In another aspect, a method for providing scalable architectures for performing repricing analyses is provided. The method is performed by a query processing server in communication with a frontend server including a frontend server processor and a frontend server memory. The query processing server is further in communication with a repricing database server including a repricing database processor and a repricing database memory. The query processing server includes a query processing server processor and a query processing server memory. The query processing server includes a gateway platform for processing communications and a repricing engine. The method includes receiving, at a gateway platform, a repricing request from the frontend server. The repricing request includes a set of scenario data associated with a repricing scenario. The set of scenario data includes a set of pricing rules and a set of conditional assumptions. The set of pricing rules and the set of conditional assumptions include corresponding timings. The method also includes defining a set of repricing periods based on the corresponding timings for the pricing rules and the set of conditional assumptions. The method further includes transmitting a creation instruction to the repricing database server to create a repricing status database defined based on the set of scenario data and the set of repricing periods. The method also includes determining a set of claims data queries for execution based on the set of scenario data. The method additionally includes querying the repricing database server with the set of claims data queries. The method further includes receiving a set of claims data responses responsive to the set of claims data queries. Upon receiving the set of claims data responses, the method includes transmitting an update instruction to the repricing status database based on the set of claims data responses. Upon determining that the repricing status database indicates that the repricing is complete, the method includes performing a repricing analysis using the set of claims data responses and the set of repricing periods.

In yet another aspect, a query processing server for providing scalable architectures in repricing is provided. The query processing server includes a query processing server processor and a query processing server memory. The query processing server includes a gateway platform for processing communications and a repricing engine. The query processing server is in communication with a frontend server including a frontend server processor and a frontend server memory, and further in communication with a repricing database server including a repricing database processor and a repricing database memory. The query processing server processor is configured to receive, at the gateway platform, a repricing request from the frontend server. The repricing request includes a set of scenario data associated with a repricing scenario. The set of scenario data includes a set of pricing rules and a set of conditional assumptions. The set of pricing rules and the set of conditional assumptions include corresponding timings. The query processing server processor is also configured to define a set of repricing periods based on the corresponding timings for the pricing rules and the set of conditional assumptions. The query processing server processor is further configured to transmit a creation instruction to the repricing database server to create a repricing status database defined based on the set of scenario data and load a queue with the set of repricing periods. The query processing server processor is also configured to determine a set of claims data queries for execution based on the set of scenario data. The query processing server processor is further configured to read from the repricing period queue and query the repricing database server with the set of claims data queries. The query processing server processor is also configured to receive a set of claims data responses responsive to the set of claims data queries. Upon receiving the set of claims data responses, the query processing server processor is further configured to transmit an update instruction to the repricing status database based on the set of claims data responses. Upon determining that the repricing status database indicates that the repricing is complete, the query processing server processor is configured to perform a repricing analysis using the set of claims data responses and the set of repricing periods.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein.

In the drawings, reference numbers may be reused to identify similar and/or identical elements.

DETAILED DESCRIPTION

Figure 1:
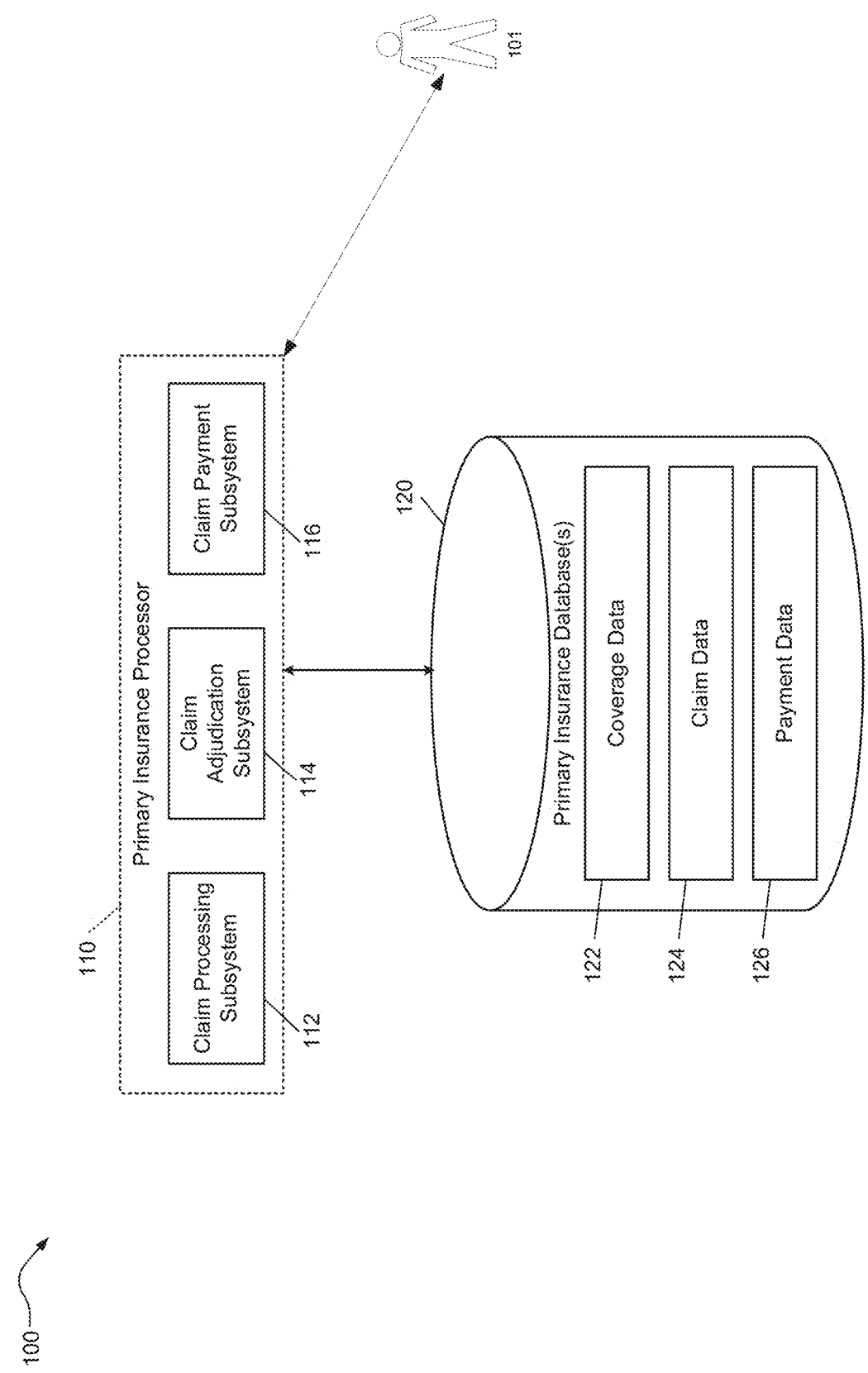
FIG. 1 is a functional block diagram of an example insurance claim processing system.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

As described above, many distributed system architectures have significant problems for scaling and providing throughput and concurrency. Because these distributed system architectures are often used with crucial business applications such as pricing tools, these scalability limitations are particularly problematic because they prevent the business applications from being scaled or expanded and used in a manner that meets the goal of business teams. Rather, business tools frequently face problems related to CPU-binding, excess memory utilization, blocking at the network level, and blocking at the I/O level. At the user level, these challenges manifest in failure of business tools to execute completely, reliably, or at all.

In view of the above technological challenges, systems and methods are desired for improving distributed system architectures to allow for increased concurrency, throughput, and scaling and to provide implementations of idempotent and asynchronous logic for use in with query intensive business tools including repricing and pricing applications.

The systems and methods described overcome known deficiencies in previous technological approaches. Specifically, by using distributed architecture for the repricing processes, the systems and methods allow for increased concurrency and scaling. By implementing idempotent and asynchronous logic for queries and repricing, the systems and methods described resolve throughput problems. By using distributed computing for queries, the systems and methods allow concurrent repricing is not ever blocked by network or database I/O. Further, because the systems and methods do not require loading of an entire claim data set into memory at once, the system avoids memory issues and can utilize smaller, cheaper compute instances.

In one aspect, the systems and methods described rely on available computing power available over a network that can receive repricing requests and respond to them in a distributed fashion. Thus, the systems and methods solve the technical problems posed by scalability, throughput, and concurrency limitations of known data architectures by improving computing performance directly. These improvements further benefit business tools by allowing allows users to input a complex set of assumptions related to parameters and variables. For example, using the systems and methods described users can input complex assumptions about the future for repricing applications and project potential costs if, for example, an insurer were to accept a given contract with a hospital, provider group or system. In one aspect, an application programming interface ("API") client may await repricing request messages. When the repricing request is made, distributed computing systems may make data queries, populate a cache, and send messages to indicate what work needs to be done. A repricing engine computing server receives these messages, applies the rules provided by the request, and loads various data stores. Using the modified data architecture, the repricing engine computing server processes the messages across complex data sets using the cache model and may process hundreds of thousands, or millions, of queries without diminished quality in performance.

The technological solutions described herein provide improvements over known prior solutions that entailed manual user interaction to analyze business requests and process them, thereby failing to address the scalability issues that underlie the performance issues in a meaningful manner. The technological solutions necessarily improve computing technology and computing networks by conferring improved scaling, throughput, and processing for data networks, and secondarily by enhancing the value of business tools to provide essential functions including repricing and pricing across complex data sets.

In one example, the systems and methods described herein provide scalable architectures that may be used to support financial tools including a contract negotiation tool. For illustrative purposes, the following description of the contract negotiation tool is provided to elaborate on the benefits that the scalable architectures may provide to that tool. In other examples, other tools may benefit from these scalable architectures. The contract negotiation tool is a web-based software program that allows users to input a complex set of assumptions about the future and project a business's potential costs assuming a given contract. In one example, the contract negotiation tool is used by an insurance company and may simulate contracts between the insurer and, for example, a hospital, provider group, or a healthcare system. The purpose of the contract negotiation tool is to simulate various scenarios with the contract including, for example, varying medical utilization levels based on the new contract(s) and their financial impact to the insurer and other parties. In order for the contract negotiation tool to function in the example of an insurance company, historical claim data is used. The historical claim data is data from previously filed insurance claims relevant to the parties in the contract and therefore includes historical claim records describing medical utilization under the contract. The historical claim data may include pricing information for medical utilization, dates associated with the historical claims, codes and descriptions identifying the claim types and categories, and codes and descriptions identifying the providers of services related to each historical claim. The contract negotiation tool receives the historical claims data and reprices it based on assumptions for a new contract or contracts. The contract negotiation tool performs the repricing process by defining logic and rules for pricing based on the new contract or contracts. The contract negotiation tool also applies the logic and rules for pricing. In at least some examples, the contract negotiation tool utilizes a claims repricing engine (or pricing engine) that processes historical claims data, defines logic and rules for pricing, and applies the logic and rules for pricing to the historical claims data. In some examples, the claims repricing engine is written in a suitable software language such as Python, hosted on a web services environment (e.g., Amazon Web Services ("AWS")), and utilizes a web framework such as Django. The claims repricing engine functionally provides some or substantially all of the core backend functionality for the contract negotiation tool. As described below, using conventional architectures, the claims repricing engine experiences scalability and throughput challenges that are addressed using the systems and methods described herein.

In some examples, logic and rules for pricing is simple but in many cases, the logic and rules for pricing are complex because the underlying contractual rules are complex. As such, the contract negotiation tool necessarily is capable of handling such complex rules in order to provide theoretical price modeling which is the output provided by the claims repricing engine and the contract negotiation tool. Business analysts frequently utilize the contract negotiation tool by iteratively adjusting the logic and rules for pricing associated with a new contract, and therefore simulate many variations to the new contract. The business analysts can then identify a preferred set or sets of contracts based on the results of pricing out the various contracts. Similarly, the business analysts can identify variations of the contracts that are particularly risky or likely to result in adverse results for the insurance company. By taking these steps, the business analysts can help limit departures from previous cost trends based on variant new contract terms.

A key feature of the contract negotiation tool is a "timeline" that allows business analysts to define assumptions of future events, pricing and logic, and any other assumptions that may affect pricing (or repricing) within time "windows" (i.e., ranges of dates and/or times in which the events or assumptions should be made). Thus, different timelines may include windows associated with particular contract rules. Further, the windows may be differently defined in different timelines such that the windows may variously interleave, overlap, or match up. As a result, particular logic and rules for pricing within a window on a timeline may be associated with multiple different sets of assumptions within corresponding windows on the assumptions timeline, or vice versa. As a result, processing varying logic and rules and assumptions is a complex undertaking that can heavily utilize or burden the technical resources of the system architecture on which the claims repricing engine and contract negotiation tool run. Adding to such complexity is the sheer volume of historical claims data and logic and rules used in many cases. In several examples, the claims repricing engine and contract negotiation tool may perform thousands of repricing calculations that each use hundreds of thousands of rows of historical claims data and hundreds or thousands of corresponding logical definitions or rules definitions. In such cases, repricing a single contract can entail processing and using hundreds of millions of records historical claims data and performing billions of subsequent computations to model repricing. As a result, the ability to scale effectively and provide high throughput and efficiency is critical.

The existing architectures failed to provide such scalability, efficiency, and throughput. First, the contract negotiation tool employs direct requests to the claims repricing engine which results in heavy utilization of system resources given the volume of repricing queries necessary to perform processing and repricing of the hundreds of millions or billions of historical claim records. Second, as a consequence of these direct requests, the contract negotiation tool (and, more specifically, the claims repricing engine) is CPU bound. ("CPU bound" as used herein means that the rate at which a process progresses is limited by the speed of available CPUs.) Third, the systems heavily burden or overuse all available resources including memory, network capacity, and web services and web framework resources. Fourth, it is difficult or impossible to determine the state of a large repricing request because the time to complete the request cannot easily be derived.

Accordingly, the systems and methods described herein address these challenges in several ways. First, the systems and methods utilize pre-caching of claim queries and, particularly common claim queries that are frequently run. Second, the systems and methods break or subdivide repricing periods into smaller component periods to more efficiently execute each repricing. Third, to manage the state of the repricing, the systems and methods monitor and maintain the state of the overall repricing. This allows users to be informed about the status of the repricing and, if the repricing is interrupted, to allow for continuity of the repricing without restarting or duplicating repricing calculations. Fourth, the systems and methods may utilize streaming of queries to reduce memory utilization. Fifth, the systems and methods use concurrency to allow for more efficient processing.

Functionally, the computing network described herein performs these tasks by (a) splitting queries and repricing logic for separate processing; (b) maintaining and utilizing pre-cached claim queries; (c) defining scenario data explaining assumptions and using the scenario data to trigger queries in order to reduce invokes and queue message sizes; (d) batching historical claims data retrieval; (e) using a gateway at a query processing server to identify needed historical claims data; (f) employing the query processing server to stream queries and query results; (g) controlling the volume of historical claims data present in memory; and (h) using the gateway to define a repricing state record and updating the repricing state record during processing.

In one example, a computing network for providing scalable architectures is provided. The computing network can be used to provide scalability to a variety of applications including but not limited to repricing applications such as the contract negotiation tool. The computing network includes a frontend server such as a web server, a query processing server, and a repricing database server. The query processing server includes a gateway platform and a repricing engine. The frontend server creates (or writes) a set of scenario data. In the example embodiment, the scenario data defines a repricing event and includes logic and rules for (re)pricing and assumptions for conditions of the repricing event, along with timing for the logic and rules and assumptions. The frontend server also instructs the repricing database server to create a repricing status database defining the repricing activity. The repricing status database is used, as described above and herein, to monitor the status of the repricing process.

Based on creating (or writing) the set of scenario data, the frontend server is configured to trigger a request to a gateway at a query processing server. The request is generated based on the set of scenario data. In the example embodiment, the request is a (re)pricing request and includes the set of scenario data associated with the (re) pricing event. In the example embodiment, based on the request, the query processing server defines a set of repricing periods created based on the timing associated with the logic and rules and assumptions. Based on creating (or writing) the set of repricing periods, the gateway at the query processing server is configured to transmit a request for a set of repricing batches. The gateway platform at the query processing server is also configured to perform a set of queries for historical claims data defined based on the scenario data. The gateway platform is further configured to write responses to the set of queries to a claims cache obtained from the claims repricing engine located on the query processing server. The claims repricing engine at the query processing server performs a poll of the set of repricing batches and identifies instructions for repricing. Based on the responses to the set of queries and the polled set of repricing batches, the repricing engine at the query processing server processes through the repricing batches and progresses through repricing. In at least some examples, as the repricing engine progresses through the repricing engine, it updates the repricing status database located at the repricing database server. Using this approach, the claims repricing engine does not require checking or readdressing and thereby avoids using memory for these steps, saving memory for repricing and other processes.

Generally, the systems and methods described herein are configured to perform at least the following steps: receiving, at a gateway platform, a repricing request from the frontend server, wherein the repricing request includes a set of scenario data associated with a repricing scenario, wherein the set of scenario data includes a set of pricing rules and a set of conditional assumptions, wherein the set of pricing rules and the set of conditional assumptions include corresponding timings; defining a set of repricing periods based on the corresponding timings for the pricing rules and the set of conditional assumptions; transmitting a creation instruction to the repricing database server to create a repricing status database defined based on the set of scenario data and the set of repricing periods; determining, at the query processing server, a set of claims data queries for execution based on the set of scenario data; querying the repricing database server with the set of claims data queries; receiving a set of claims data responses responsive to the set of claims data queries; upon receiving the set of claims data responses, transmitting an update instruction to the repricing status database based on the set of claims data responses; upon determining that the repricing status database indicates that the repricing is complete, performing a repricing analysis using the set of claims data responses and the set of repricing periods; continually polling the repricing status database to determine a state of the repricing; determining whether the repricing status database indicates that the repricing is complete based on the polling; determining that the repricing process has been interrupted; polling the repricing status database to determine a state of the repricing prior to interruption; determining a set of unperformed claims data queries based on the state of the repricing prior to interruption; querying the repricing database server with the set of unperformed claims data queries; receiving a second set of claims data responses responsive to the set of unperformed claims data queries; upon determining that the repricing status database indicates that the repricing is complete, performing a repricing analysis using the set of claims data responses, the second set of claims data responses, and the set of repricing periods; subdividing the set of repricing periods into corresponding sets of component repricing periods in order to more efficiently execute each repricing; upon determining that the repricing status database indicates that the repricing is complete, performing a repricing analysis using the set of claims data responses and the subdivided set of repricing periods; listening to the repricing period queue; querying the repricing database server with the set of claims data queries using streaming to reduce memory utilization by the query processing server; identifying a set of claims data queries which are frequently run as common queries; querying the repricing database server with the common queries; receiving a set of common claims data responses responsive to the common queries; pre-caching the set of common claims data responses; determining, at the query processing server, that the set of claims data queries for execution includes a portion of claims data queries that are common queries; and obtaining a portion of claims data responses responsive to the portion of claims data queries from pre-cache.

FIG. 1 is a functional block diagram of an example insurance claim processing system 100 including a primary insurance processor system 110. Primary insurance processor system 110 includes subsystems 112, 114, and 116 capable of providing claim processing, claim adjudication, and claim payment respectively. Specifically, primary insurance processor system 110 is associated with a corresponding primary insurance database system 120. As described above and herein, database systems such as database systems 120 may include one or more than one databases that each are configured to use a DBMS. In some cases the DBMS systems may be distinct from one another. Further, each database is associated with a data schema that may be unique depending on whether the DBMS and claim category are distinct. As such, the databases include data that cannot be processed using common programs. Database systems 120 include necessary information stored on at least one of their underlying databases. Specifically, primary insurance database system 120 includes coverage data 122, claim data 124, and payment data 126.

Figure 2:
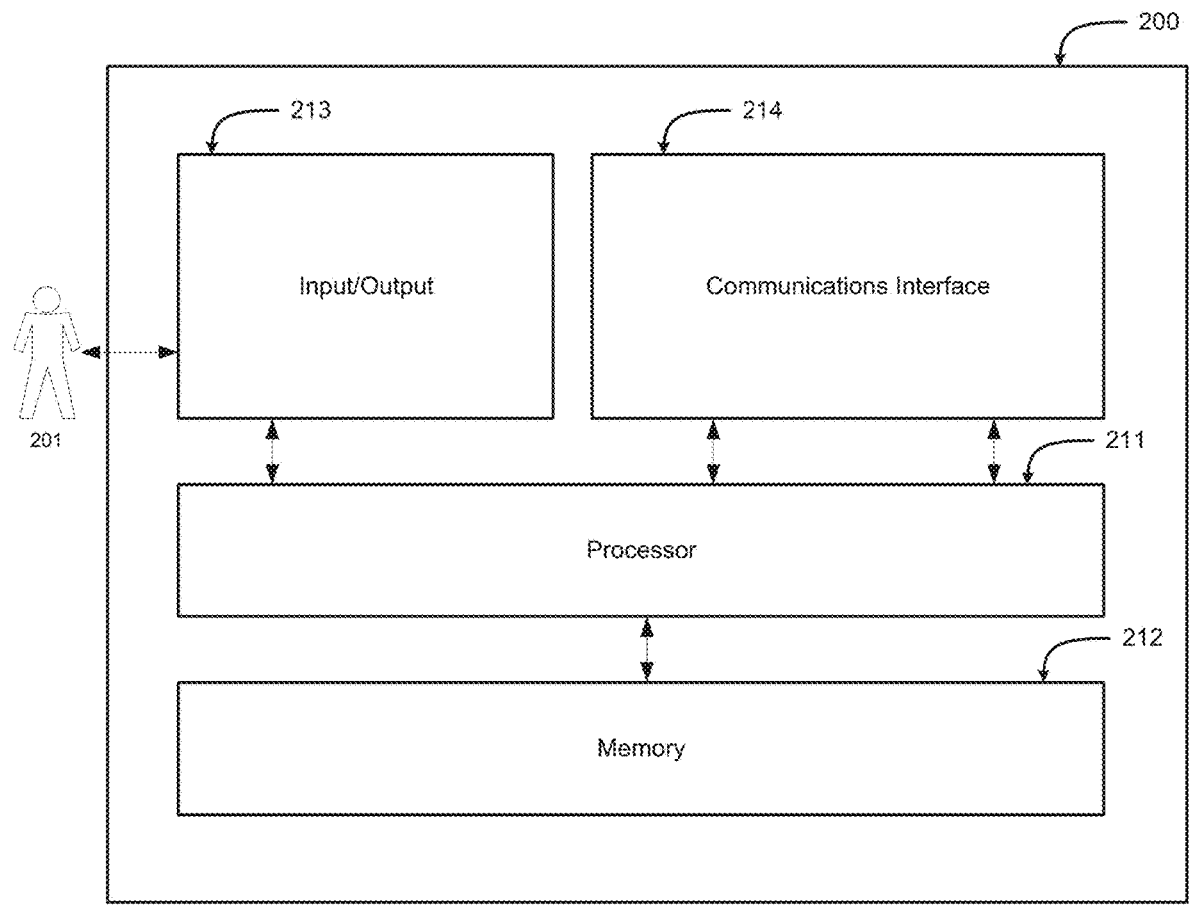
FIG. 2 is a functional block diagram of an example computing device that may be used in the computing network for providing scalable architectures described.
Figure 3:
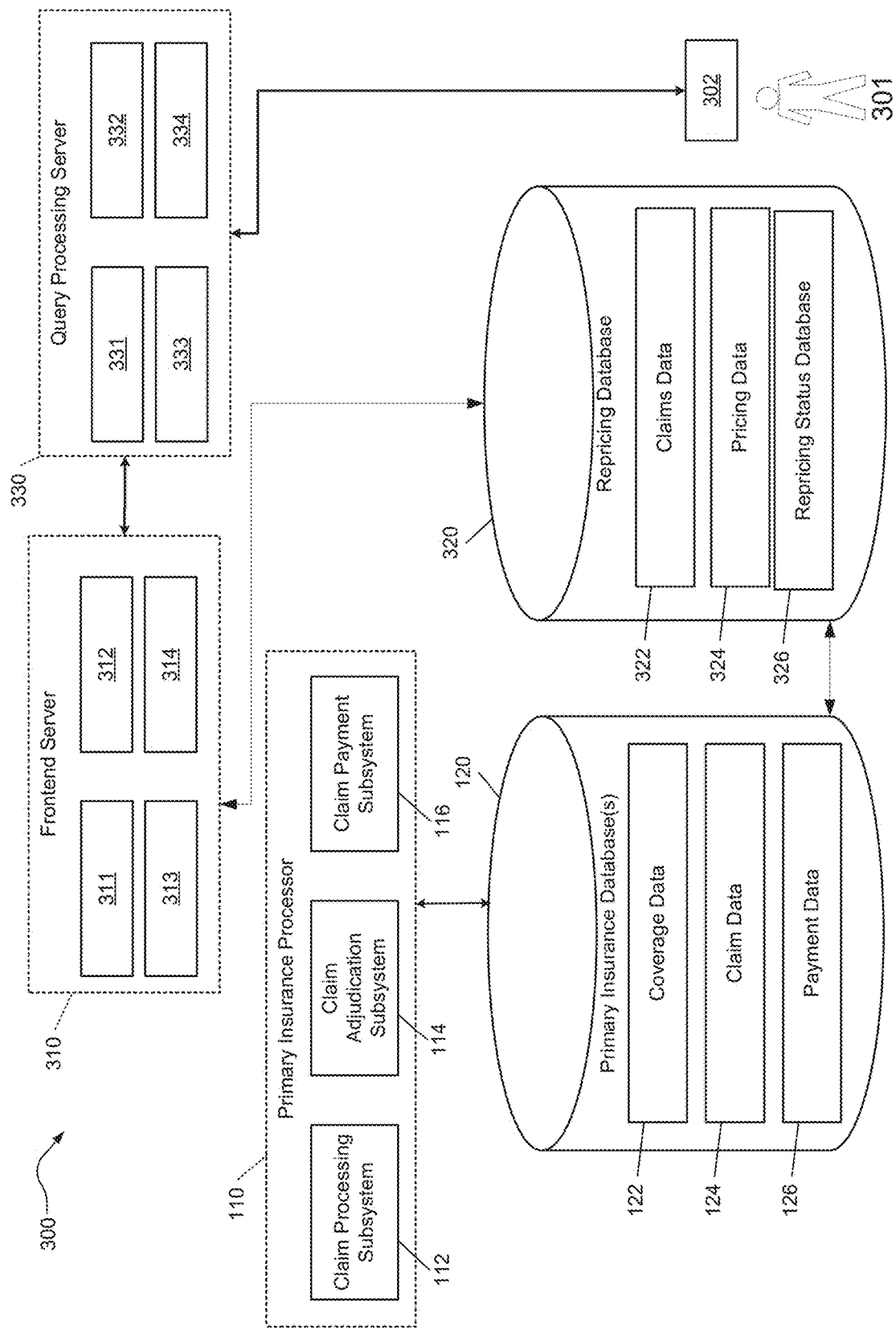
FIG. 3 is a functional block diagram of a computing network for providing scalable architectures that may be deployed within the system of FIG. 1 using the computing devices shown in FIG. 2.

FIG. 2 is a functional block diagram of an example computing device that may be used in the method for providing scalable architectures for performing repricing analyses described, and may represent the query processing server, frontend server and/or repricing database server (all shown in FIG. 3). Specifically, computing device 200 illustrates an example configuration of a computing device for the systems shown herein, and particularly in FIGS. 1 and 3. Computing device 200 illustrates an example configuration of a computing device operated by a user 201 in accordance with one embodiment of the present invention. Computing device 200 may include, but is not limited to, the query processing server, frontend server and/or repricing database server (all shown in FIG. 3), other user systems, and other server systems. Computing device 200 may also include servers, desktops, laptops, mobile computing devices, stationary computing devices, computing peripheral devices, smart phones, wearable computing devices, medical computing devices, and vehicular computing devices. In some variations, computing device 200 may be any computing device capable of the described method for providing scalable architectures for performing repricing analyses. In some variations, the characteristics of the described components may be more or less advanced, primitive, or non-functional.

In an example embodiment, computing device 200 includes a processor 211 for executing instructions. In some embodiments, executable instructions are stored in a memory area 212. Processor 211 may include one or more processing units, for example, a multi-core configuration. Memory area 212 is any device allowing information such as executable instructions and/or written works to be stored and retrieved. Memory area 212 may include one or more computer readable media.

Computing device 200 also includes at least one input/output component 213 for receiving information from and providing information to user 201. In some examples, input/output component 213 may be of limited functionality or non-functional as in the case of some wearable computing devices. In other examples, input/output component 213 is any component capable of conveying information to or receiving information from user 201. In some embodiments, input/output component 213 includes an output adapter such as a video adapter and/or an audio adapter. Input/output component 213 may alternatively include an output device such as a display device, a liquid crystal display (LCD), organic light emitting diode (OLED) display, or "electronic ink" display, or an audio output device, a speaker or headphones. Input/output component 213 may also include any devices, modules, or structures for receiving input from user 201. Input/output component 213 may therefore include, for example, a keyboard, a pointing device, a mouse, a stylus, a touch sensitive panel, a touch pad, a touch screen, a gyroscope, an accelerometer, a position detector, or an audio input device. A single component such as a touch screen may function as both an output and input device of input/output component 213. Input/output component 213 may further include multiple sub-components for carrying out input and output functions.

Computing device 200 may also include a communications interface 214, which may be communicatively coupleable to a remote device such as a remote computing device, a remote server, or any other suitable system. Communication interface 214 may include, for example, a wired or wireless network adapter or a wireless data transceiver for use with a mobile phone network, Global System for Mobile communications (GSM), 3G, 4G, or other mobile data network or Worldwide Interoperability for Microwave Access (WIMAX). Communications interface 214 is configured to allow computing device 200 to interface with any other computing device or network using an appropriate wireless or wired communications protocol such as, without limitation, BLUETOOTH®, Ethernet, or IEE 802.11. Communications interface 214 allows computing device 200 to communicate with any other computing devices with which it is in communication or connection.

FIG. 3 is a functional block diagram of a computing network for providing scalable architectures 300 that may be deployed within the system 100 (shown in FIG. 1) using the computing devices 200 (shown in FIG. 2) to provide scalable architectures for use in repricing. In one example, computing network 300 includes primary insurance processor 110 (along with associated subsystems 112, 114, 116) and primary insurance database(s) 120 (along with associated data 122, 124, and 126). Computing network 300 includes frontend (web) server 310 which further includes processor 311, memory 312, input/output component 313, and communications interface 314. Computing network 300 further includes repricing database server 320 which further includes necessary components for processors, memory, input/output components, and communications interfaces, along with relevant information for performing the repricing using scalable architectures as described herein and specifically claims data 322, pricing data, 324, and a repricing status database 326. In some examples, claims data 322 and pricing data 324 further includes records on frequency of querying of such information to allow query processing server 330 to identify such data as frequently queried, and to identify common queries that are pre-cached in memory 332 or in another suitable location. Repricing status database 326 is configured to allow for tracking of the process of repricing. In an example embodiment, frontend (web) server 310 writes scenario data to query processing server 330 and triggers gateway platform at query processing server 330 to create an entry at the repricing database server 320 for a repricing status database 326. During repricing, query processing server 330 updates repricing status database 326 and polls it to monitor the status of repricing. Computing network 300 further includes query processing server 330 which further includes processor 331, memory 332, input/output component 333, and communications interface 334. In some examples, query processing server 330 includes a gateway platform for processing communications and a repricing engine for performing repricing. Query processing server 330 may also include a query processing platform for managing the processes performed by query processing server 330.

Figure 4:
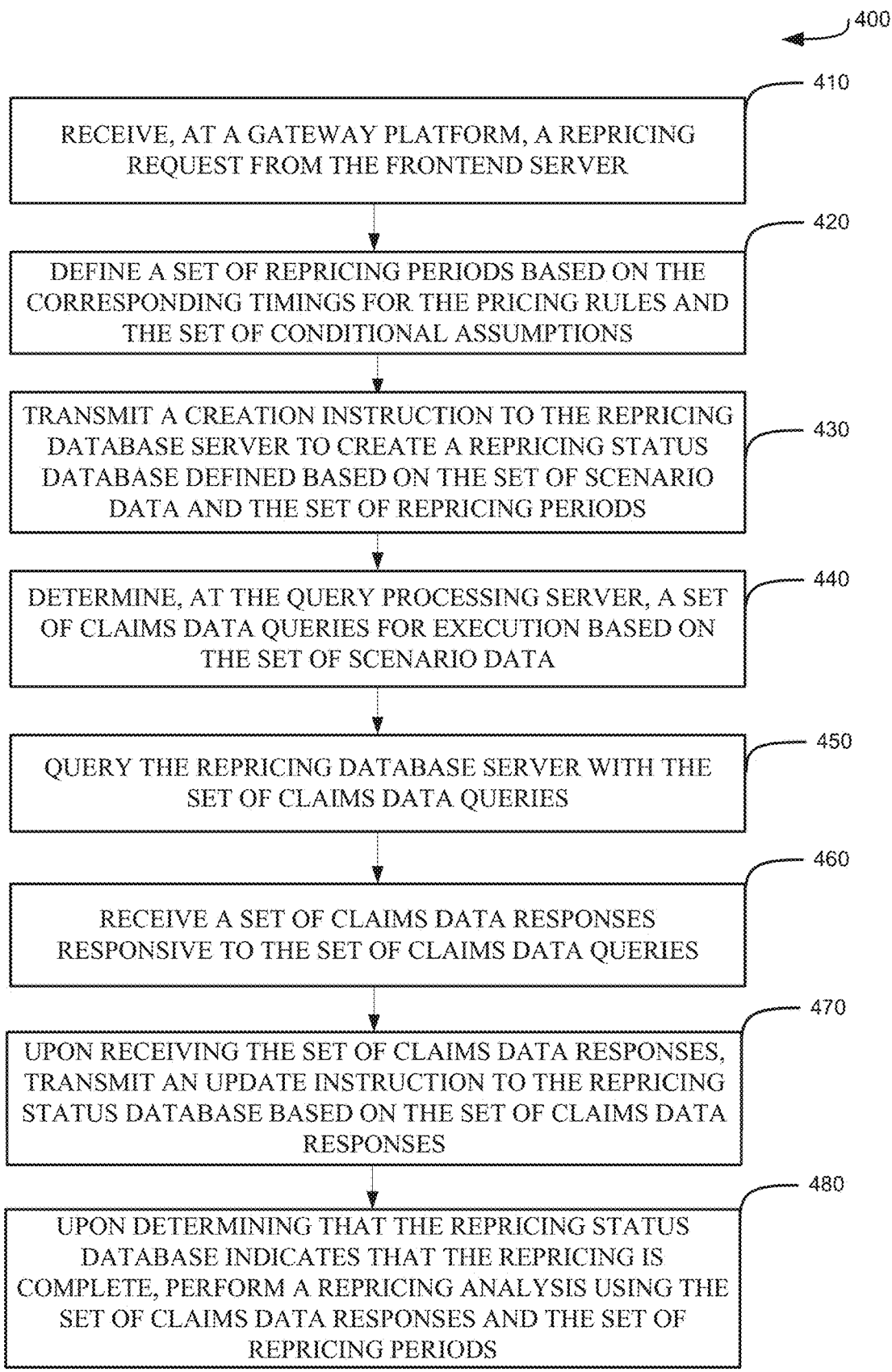
FIG. 4 is a flow diagram representing an example method for providing scalable architectures for performing repricing analyses from the perspective of the query processing server shown in FIG. 3.

FIG. 4 is a flow diagram 400 representing an example method for providing scalable architectures for performing repricing analyses performed by a query processing server 330 (shown in FIG. 3). Query processing server 330 is configured to receive 410, at a gateway platform, a repricing request from the frontend server. The repricing request includes a set of scenario data associated with a repricing scenario. The set of scenario data includes a set of pricing rules and a set of conditional assumptions. The set of pricing rules and the set of conditional assumptions include corresponding timings. Query processing server 330 is also configured to define 420 a set of repricing periods based on the corresponding timings for the pricing rules and the set of conditional assumptions. Query processing server 330 is further configured to transmit 430 a creation instruction to the repricing database server to create a repricing status database defined based on the set of scenario data and the set of repricing periods. Query processing server 330 is also configured to determine 440 a set of claims data queries for execution based on the set of scenario data. Query processing server 330 is also configured to query 450 the repricing database server with the set of claims data queries. Query processing server 330 is further configured to receive 460 a set of claims data responses responsive to the set of claims data queries. Upon receiving the set of claims data responses, query processing server 330 is configured to transmit 470 an update instruction to the repricing status database based on the set of claims data responses. Upon determining that the repricing status database indicates that the repricing is complete, query processing server 330 is configured to perform 480 a repricing analysis using the set of claims data responses and the set of repricing periods.

Figure 5:
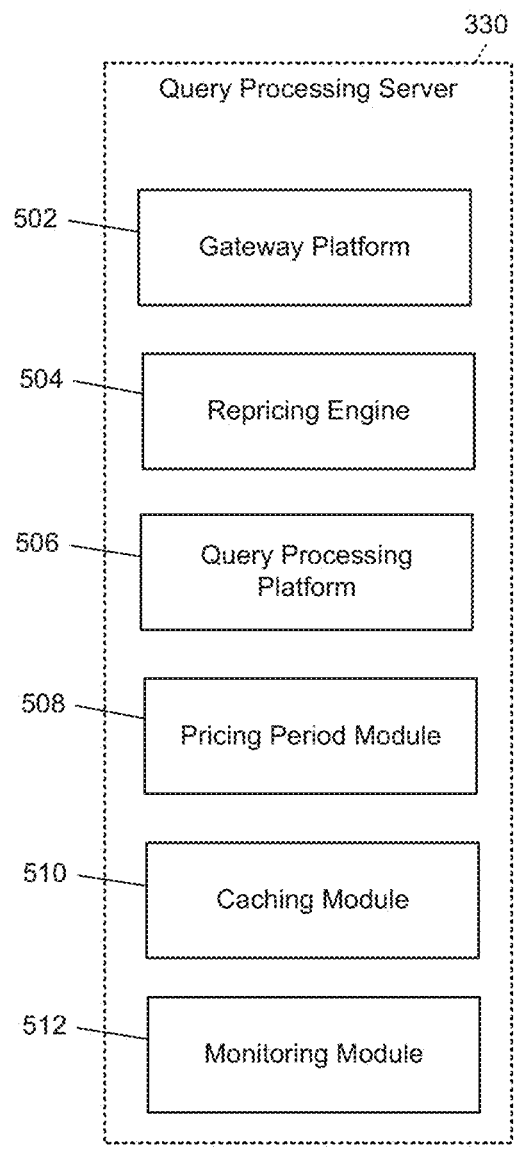
FIG. 5 is a diagram of elements of one or more example computing devices that may be used in the system shown in FIGS. 1 and 3.

FIG. 5 is a diagram of elements 502, 504, 506, 508, 510, and 512, of one or more example computing devices that may be used in the system 300 (shown in FIG. 3). Query processing server 330 includes gateway platform 502, repricing engine 504, query processing platform 506, caching module 508, and monitoring module 510. Gateway platform 502 is configured to receive and manage communications between query processing server 330 and other devices including frontend server 310 and repricing database server 320. Repricing engine 504 may be configured to perform the repricing methods described herein and, more specifically, to parse scenario data, process scenario data, identify pricing rules, conditional assumptions, corresponding timings, and perform repricing. Query processing platform 506 may also be configured to perform steps including identifying relevant queries to perform, identifying common queries, performing queries, and caching common queries. Pricing period module 508 is configured to identify, divide, and subdivide repricing periods. Caching module 510 is configured to provide and manage precached data from common queries. Monitoring module 512 is configured to monitor the repricing status database 326.

Figure 6:
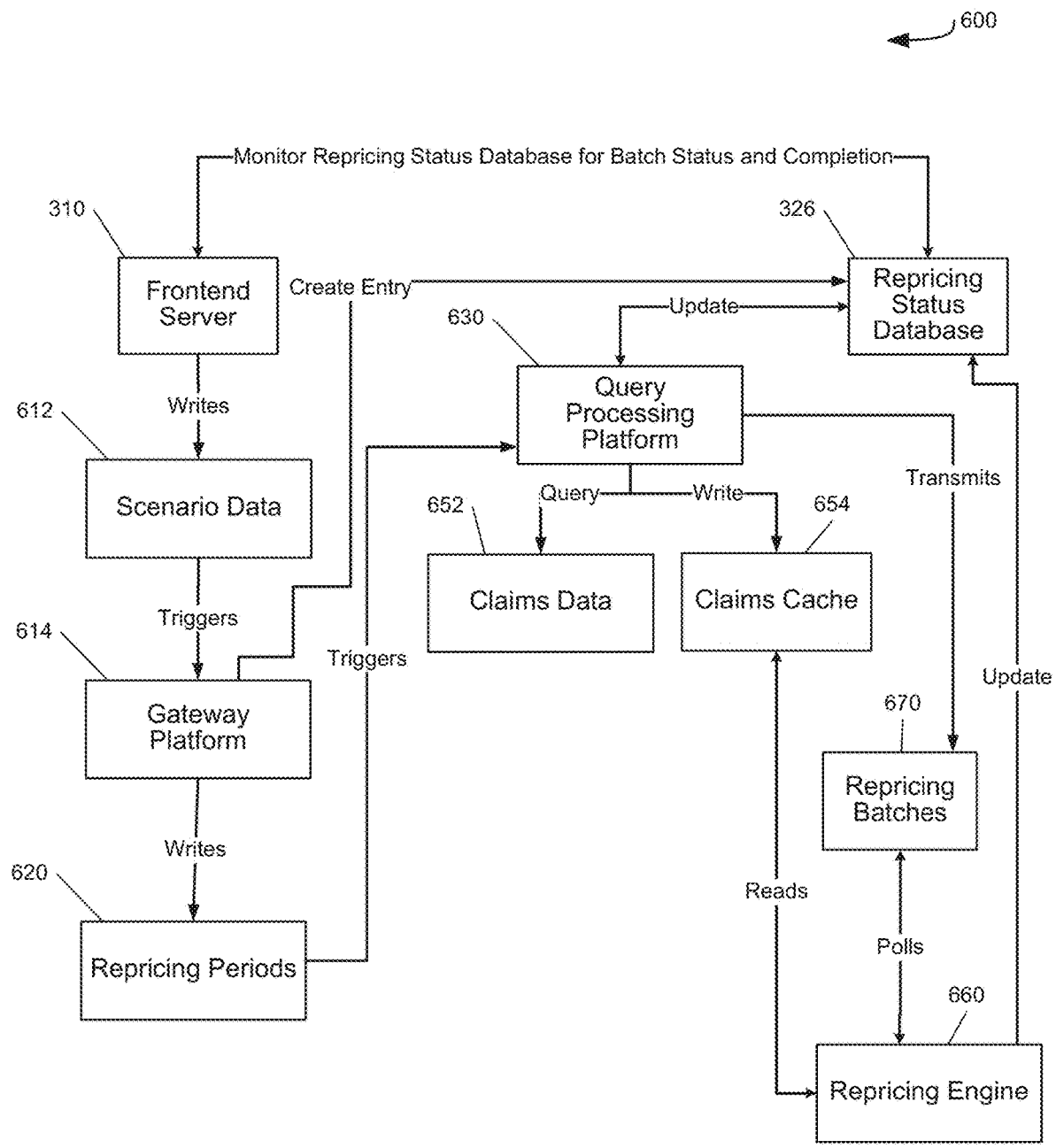
FIG. 6 is a flow diagram of an example providing scalable architectures for performing repricing analyses from the perspective of the query processing server shown in FIG. 3.

FIG. 6 is a flow diagram 600 of an example providing scalable architectures for performing repricing analyses from the perspective of the query processing server 330 (shown in FIG. 3). In operation, frontend server 310 receives a request for a repricing from a user (not shown) and writes scenario data 612 and transmits such scenario data 612 to trigger gateway platform 614 to initiate repricing. Gateway platform 614 is located at query processing server 330 (shown in FIG. 3) and defines (or writes) a set of repricing periods 620 based on the corresponding timings for each of the pricing rules and the set of conditional assumptions. Gateway platform 614 also creates an entry at repricing status database 326 for the repricing event. The entry is used to define the repricing event at repricing status database 326 and allow query processing server 330 to monitor the status of repricing. When gateway platform 614 writes the set of repricing periods 620 it triggers query processing platform 630 to perform several steps. In one example, query processing platform 630 is located at query processing server 330. In one aspect, query processing platform 630 (or an equivalent module) queries for claims data 652. In one example, querying for claims data 652 is performed by querying repricing database server 320 for claims data 322 or pricing data 324. In another aspect, query processing platform 630 determines it is performing common queries and precaches (or writes) the results of such queries to claims cache 654. In some examples, when the query processing platform 630 has written such responses or results to claims cache 654, the query processing platform 630 determines that a common query (or queries) is requested and reads from the claims cache 654 rather than querying claims data 652. In many examples, repricing engine 660 manages the process of reading from claims cache 652 or queries of claims data 652 and further utilizes defined repricing batches 670 to simplify the complexity of performing the repricing. Further, repricing engine 660 and query processing platform 630 continually update repricing status database 326 to allow the repricing to be tracked and monitored. In one example, users may determine the status of the repricing based on such tracking. In another example, if the repricing is interrupted, the query processing server 330 is configured to restart based on the tracked status. As such, frontend server 310 allows a user to monitor repricing status and batch processing status.

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A. The term subset does not necessarily require a proper subset. In other words, a first subset of a first set may be coextensive with (equal to) the first set.

In this application, including the definitions below, the term "module" or the term "controller" may be replaced with the term "circuit." The term "module" may refer to, be part of, or include processor hardware (shared, dedicated, or group) that executes code and memory hardware (shared, dedicated, or group) that stores code executed by the processor hardware.

The module may include one or more interface circuits. In some examples, the interface circuit(s) may implement wired or wireless interfaces that connect to a local area network (LAN) or a wireless personal area network (WPAN). Examples of a LAN are Institute of Electrical and Electronics Engineers (IEEE) Standard 802.11-2016 (also known as the WIFI wireless networking standard) and IEEE Standard 802.3-2015 (also known as the ETHERNET wired networking standard). Examples of a WPAN are the BLUETOOTH wireless networking standard from the Bluetooth Special Interest Group and IEEE Standard 802.15.4.

The module may communicate with other modules using the interface circuit(s). Although the module may be depicted in the present disclosure as logically communicating directly with other modules, in various implementations the module may actually communicate via a communications system. The communications system includes physical and/or virtual networking equipment such as hubs, switches, routers, and gateways. In some implementations, the communications system connects to or traverses a wide area network (WAN) such as the Internet. For example, the communications system may include multiple LANs connected to each other over the Internet or point-to-point leased lines using technologies including Multiprotocol Label Switching (MPLS) and virtual private networks (VPNs).

In various implementations, the functionality of the module may be distributed among multiple modules that are connected via the communications system. For example, multiple modules may implement the same functionality distributed by a load balancing system. In a further example, the functionality of the module may be split between a server (also known as remote, or cloud) module and a client (or, user) module.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave). The term computer-readable medium is therefore considered tangible and non-transitory. Non-limiting examples of a non-transitory computer-readable medium are nonvolatile memory devices (such as a flash memory device, an erasable programmable read-only memory device, or a mask read-only memory device), volatile memory devices (such as a static random access memory device or a dynamic random access memory device), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

The computer programs include processor-executable instructions that are stored on at least one non-transitory computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:
1. A computing network for providing scalable architectures, comprising:
    a frontend server comprising a frontend server processor and a frontend server memory;

a query processing server comprising a query processing server processor and a query processing server memory, wherein the query processing server includes a gateway platform for processing communications and a repricing engine; and a repricing database server comprising a repricing database processor and a repricing database memory, wherein the frontend server, the query processing server, and the repricing database server are all in networked communication with one another, wherein the query processing server processor is configured to:

receive, at a gateway platform, a repricing request from the frontend server, wherein the repricing request includes a set of scenario data associated with a repricing scenario, wherein the set of scenario data includes a set of pricing rules and a set of conditional assumptions, wherein the set of pricing rules and the set of conditional assumptions include corresponding timings;

define a set of repricing periods based on the corresponding timings for the pricing rules and the set of conditional assumptions;

transmit a creation instruction to the repricing database server to create a repricing status database defined based on the set of scenario data and a queue based on the set of repricing periods;

determine a set of claims data queries for execution based on the set of scenario data;

query the repricing database server with the set of claims data queries;

receive a set of claims data responses responsive to the set of claims data queries;

upon receiving the set of claims data responses, transmit an update instruction to the repricing status database based on the set of claims data responses; and upon determining that the repricing status database indicates that the repricing is complete, perform a repricing analysis using the set of claims data responses and the set of repricing periods.

2. The computing network of claim 1, wherein said query processing server processor is configured to:

continually poll the repricing status database to determine a state of the repricing; and determine whether the repricing status database indicates that the repricing is complete based on the polling.

3. The computing network of claim 1, wherein said query processing server processor is configured to:

determine that the repricing process has been interrupted;

poll the repricing status database to determine a state of the repricing prior to interruption;

determine a set of unperformed claims data queries based on the state of the repricing prior to interruption;

query the repricing database server with the set of unperformed claims data queries;

receive a second set of claims data responses responsive to the set of unperformed claims data queries; and upon determining that the repricing status database indicates that the repricing is complete, perform a repricing analysis using the set of claims data responses, the second set of claims data responses, and the set of repricing periods.

4. The computing network of claim 1, wherein said query processing server processor is configured to:

subdivide the set of repricing periods into corresponding sets of component repricing periods in order to more efficiently execute the repricing; and upon determining that the repricing status database indicates that the repricing is complete, perform a repricing analysis using the set of claims data responses and the subdivided set of repricing periods.

5. The computing network of claim 1, wherein said query processing server processor is configured to:

query the repricing database server with the set of claims data queries using streaming to reduce memory utilization by the query processing server.

6. The computing network of claim 1, wherein said query processing server processor is configured to:

identify a set of claims data queries which are frequently run as common queries;

query the repricing database server with the common queries;

receive a set of common claims data responses responsive to the common queries; and pre-cache the set of common claims data responses.

7. The computing network of claim 6, wherein said query processing server processor is configured to:

determine that the set of claims data queries for execution includes a portion of claims data queries that are common queries; and obtain a portion of claims data responses responsive to the portion of claims data queries from pre-cache.

8. A method for providing scalable architectures for performing repricing analyses performed by a query processing server in communication with a frontend server including a frontend server processor and a frontend server memory and further in communication with a repricing database server including a repricing database processor and a repricing database memory, wherein the query processing server includes a query processing server processor and a query processing server memory, wherein the query processing server includes a gateway platform for processing communications and a repricing engine, said method comprising:

receiving, at a gateway platform, a repricing request from the frontend server, wherein the repricing request includes a set of scenario data associated with a repricing scenario, wherein the set of scenario data includes a set of pricing rules and a set of conditional assumptions, wherein the set of pricing rules and the set of conditional assumptions include corresponding timings;

defining a set of repricing periods based on the corresponding timings for the pricing rules and the set of conditional assumptions;

transmitting a creation instruction to the repricing database server to create a repricing status database defined based on the set of scenario data and queue based on the set of repricing periods;

determining a set of claims data queries for execution based on the set of scenario data;

querying the repricing database server with the set of claims data queries;

receiving a set of claims data responses responsive to the set of claims data queries;

upon receiving the set of claims data responses, transmitting an update instruction to the repricing status database based on the set of claims data responses; and upon determining that the repricing status database indicates that the repricing is complete, performing a repricing analysis using the set of claims data responses and the set of repricing periods.

9. The method of claim 8, further comprising:
continually polling the repricing status database to determine a state of the repricing; and
determining whether the repricing status database indicates that the repricing is complete based on the polling.

10. The method of claim 8, further comprising:
determining that the repricing process has been interrupted;
polling the repricing status database to determine a state of the repricing prior to interruption;
determining a set of unperformed claims data queries based on the state of the repricing prior to interruption;
querying the repricing database server with the set of unperformed claims data queries;
receiving a second set of claims data responses responsive to the set of unperformed claims data queries; and
upon determining that the repricing status database indicates that the repricing is complete, performing a repricing analysis using the set of claims data responses, the second set of claims data responses, and the set of repricing periods.

11. The method of claim 8, further comprising:
subdividing the set of repricing periods into corresponding sets of component repricing periods in order to more efficiently execute the repricing; and
upon determining that the repricing status database indicates that the repricing is complete, performing a repricing analysis using the set of claims data responses and the subdivided set of repricing periods.

12. The method of claim 8, further comprising:
querying the repricing database server with the set of claims data queries using streaming to reduce memory utilization by the query processing server.

13. The method of claim 8, further comprising:
identifying a set of claims data queries which are frequently run as common queries;
querying the repricing database server with the common queries;
receiving a set of common claims data responses responsive to the common queries; and
pre-caching the set of common claims data responses.

14. The method of claim 13, further comprising:
determining that the set of claims data queries for execution includes a portion of claims data queries that are common queries; and
obtaining a portion of claims data responses responsive to the portion of claims data queries from pre-cache.

15. A query processing server for providing scalable architectures in repricing, said query processing server comprising a query processing server processor and a query processing server memory, wherein the query processing server includes a gateway platform for processing communications and a repricing engine, said query processing server in communication with a frontend server comprising a frontend server processor and a frontend server memory, said query processing server further in communication with a repricing database server comprising a repricing database processor and a repricing database memory, wherein the query processing server processor is configured to:
receive, at a gateway platform, a repricing request from the frontend server, wherein the repricing request includes a set of scenario data associated with a repricing scenario, wherein the set of scenario data includes a set of pricing rules and a set of conditional assumptions, wherein the set of pricing rules and the set of conditional assumptions include corresponding timings;
define a set of repricing periods based on the corresponding timings for the pricing rules and the set of conditional assumptions;
transmit a creation instruction to the repricing database server to create a repricing status database defined based on the set of scenario data and a queue based on the set of repricing periods;
determine a set of claims data queries for execution based on the set of scenario data;
query the repricing database server with the set of claims data queries;
receive a set of claims data responses responsive to the set of claims data queries;
upon receiving the set of claims data responses, transmit an update instruction to the repricing status database based on the set of claims data responses; and
upon determining that the repricing status database indicates that the repricing is complete, perform a repricing analysis using the set of claims data responses and the set of repricing periods.

16. The query processing server of claim 15, further configured to:
continually poll the repricing status database to determine a state of the repricing; and
determine whether the repricing status database indicates that the repricing is complete based on the polling.

17. The query processing server of claim 15, further configured to:
determine that the repricing process has been interrupted;
poll the repricing status database to determine a state of the repricing prior to interruption;
determine a set of unperformed claims data queries based on the state of the repricing prior to interruption;
query the repricing database server with the set of unperformed claims data queries;
receive a second set of claims data responses responsive to the set of unperformed claims data queries; and
upon determining that the repricing status database indicates that the repricing is complete, perform a repricing analysis using the set of claims data responses, the second set of claims data responses, and the set of repricing periods.

18. The query processing server of claim 15, further configured to:
subdivide the set of repricing periods into corresponding sets of component repricing periods in order to more efficiently execute the repricing; and
upon determining that the repricing status database indicates that the repricing is complete, perform a repricing analysis using the set of claims data responses and the subdivided set of repricing periods.

19. The query processing server of claim 15, further configured to:
query the repricing database server with the set of claims data queries using streaming to reduce memory utilization by the query processing server.

20. The query processing server of claim 15, further configured to:
identify a set of claims data queries which are frequently run as common queries;
query the repricing database server with the common queries;
receive a set of common claims data responses responsive to the common queries;

pre-cache the set of common claims data responses;
determine that the set of claims data queries for execution includes a portion of claims data queries that are common queries; and
obtain a portion of claims data responses responsive to the portion of claims data queries from pre-cache.

\* \* \* \* \*